US 6,583,316 B1

(12) United States Patent
Onodera et al.

(10) Patent No.: US 6,583,316 B1
(45) Date of Patent: Jun. 24, 2003

(54) CATALYSTS FOR PRODUCTION OF UNSATURATED ALDEHYDE AND UNSATURATED CARBOXYLIC ACID AND A PROCESS FOR PRODUCING UNSATURATED ALDEHYDE AND UNSATURATED CARBOXYLIC ACID USING THE CATALYSTS

(75) Inventors: Hideo Onodera, Himeji (JP); Michio Tanimoto, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 09/568,975

(22) Filed: May 11, 2000

(30) Foreign Application Priority Data

May 13, 1999 (JP) ............................................. 11-132462

(51) Int. Cl.[7] ............................................. C07C 51/16
(52) U.S. Cl. ....................... 562/537; 562/538; 562/545; 562/546; 502/325
(58) Field of Search ........................... 502/325; 562/537, 562/538, 545, 546

(56) References Cited

U.S. PATENT DOCUMENTS

| 4,001,317 A | | 1/1977 | Grasselli et al. |
|---|---|---|---|
| 4,024,074 A | * | 5/1977 | Cairati et al. |
| 4,219,484 A | | 8/1980 | Milberger et al. |
| 4,250,339 A | * | 2/1981 | Sakamoto et al. |
| 4,414,134 A | * | 11/1983 | Friedrich et al. |
| 4,511,671 A | | 4/1985 | Saito et al. |
| 4,537,874 A | | 8/1985 | Sato et al. |
| 4,837,360 A | | 6/1989 | Kadowaki et al. |
| 4,873,217 A | * | 10/1989 | Kawajiri et al. |
| 4,925,980 A | | 5/1990 | Matsumoto et al. |
| 5,153,162 A | | 10/1992 | Kurimoto et al. |
| 5,364,825 A | | 11/1994 | Neumann et al. |
| 5,618,974 A | | 4/1997 | Kurimoto et al. |
| 5,929,275 A | * | 7/1999 | Wada et al. |

FOREIGN PATENT DOCUMENTS

| EP | 0-456837 A1 | 11/1991 |
|---|---|---|
| EP | 0 608 917 | 8/1994 |
| JP | 552619 | 1/1980 |
| JP | 60239439 | 11/1985 |
| JP | 615043 | 1/1986 |

OTHER PUBLICATIONS

Yuichi Kase, et al., Copending application S.N. 09/557,295 filed Apr. 25, 2000.
JP 03–294239 A (Nippon Shokubai Co., Ltd) Dec. 25, 1991 (Abstract).
JP 03–170445 A (Mitsui Toatsu Chem. Inc.) Jul. 24, 1991 (Abstract).
JP 55–000358 A (Nippon Zeon KK) Jan. 5, 1980 (Abstract).

* cited by examiner

Primary Examiner—Paul J. Killos
(74) Attorney, Agent, or Firm—Sherman & Shalloway

(57) ABSTRACT

Improved catalysts for use in vapor phase oxidation of at least one compound selected from the group consisting of propylene, isobutylene, t-butanol and methyl-t-butyl ether with molecular oxygen or a molecular oxygen-containing gas to produce the corresponding unsaturated aldehyde and unsaturated carboxylic acid are provided. The improved catalysts are compositions comprising (A) a complex oxide containing as essential components molybdenum, bismuth and iron, which is known per se as a catalyst for said reaction and (B) a complex oxide containing cerium and zirconium as the essential components. When the improved catalysts are used, the production operation of unsaturated aldehyde and unsaturated carboxylic acid can be continued stably for over prolonged period.

8 Claims, No Drawings

CATALYSTS FOR PRODUCTION OF UNSATURATED ALDEHYDE AND UNSATURATED CARBOXYLIC ACID AND A PROCESS FOR PRODUCING UNSATURATED ALDEHYDE AND UNSATURATED CARBOXYLIC ACID USING THE CATALYSTS

TECHNICAL FIELD TO WHICH THE INVENTION BELONGS

This invention relates to catalysts for production of unsaturated aldehyde and unsaturated carboxylic acid and to a process for producing unsaturated aldehyde and unsaturated carboxylic acid. More particularly, the invention relates to improved catalysts for producing unsaturated aldehyde and unsaturated carboxylic acid at high yield and with stability over a prolonged period, by vapor phase oxidation of at least one compound selected from the group consisting of propylene, isobutylene, t-butanol and methyl-t-butyl ether; and also to a process for producing unsaturated aldehyde and unsaturated carboxylic acid using the improved catalysts.

CONVENTIONAL TECHNOLOGY

A number of improved catalysts have been proposed for high efficiency production of unsaturated aldehyde and unsaturated carboxylic acid by vapor phase catalytic oxidation reaction of propylene, isobutylene, t-butanol or methyl-t-butyl ether. The most of those proposed catalysts contain molybdenum, bismuth and iron as their chief components.

However, those catalysts still are subject to problems which need to be solved, in respect of yields of unsaturated aldehyde and unsaturated carboxylic acid and the catalyst life. Molybdenum in a catalyst is apt to sublime, which induces irreversible degradation in the catalytic activity. The intended oxidation reaction is extremely exothermic and in the catalyst layers, in particular, at the local abnormally high temperature zone which is referred to as hot spot, molybdenum sublime vigorously. Particularly in heavy load operation aiming at high productivity, naturally the heat accumulation at the hot spot increases to prolong the period during which the catalyst is used under high temperatures. Considering these factors, catalysts having high activity and exhibiting stable performance over a long period are in demand.

On the other hand, various proposals have been also made as to complex oxides whose essential components are cerium and zirconium. Most of these complex oxides are known as additive components to waste gas-combustion catalysts, but it is entirely unknown that such complex oxides whose essential components are cerium and zirconium exhibit effective catalytic activity in production of unsaturated aldehyde and unsaturated carboxylic acid through vapor phase catalytic oxidation of propylene, isobutylene, t-butanol or methyl-t-butyl ether, when used in combination with molybdenum-bismuth-iron-containing catalysts.

OBJECTS OF THE INVENTION

One of the objects of the present invention is to provide catalysts which are useful in production of unsaturated aldehyde and unsaturated carboxylic acid at high yield.

A further object of the present invention is to provide catalysts for unsaturated aldehyde and unsaturated carboxylic acid production, which have long catalyst life and enable stable operation over prolonged period.

Still another object of the present invention is to provide catalysts for unsaturated aldehyde and unsaturated carboxylic acid production which enable stable operation over prolonged period, even under heavy load operation aiming at high productivity.

An additional object of the present invention is to provide a process for producing unsaturated aldehyde and unsaturated carboxylic acid at high yield and with stability over prolonged period, using the above catalysts.

MEANS TO SOLVE THE PROBLEMS

We have discovered that a composition, in which a complex oxide known as catalyst for unsaturated aldehyde and unsaturated carboxylic acid production, containing molybdenum, bismuth and iron as the essential components, is combined with a complex oxide whose essential components are cerium and zirconium, exhibits high catalytic activity in the intended reaction and excellent stability; and that the use of such a composition as a catalyst in said reaction accomplishes the above objects.

Thus, according to the invention, as a catalyst for producing unsaturated aldehyde and unsaturated carboxylic acid through oxidation of at least one compound selected from the group consisting of propylene, isobutylene, t-butanol and methyl-t-butyl ether with molecular oxygen or a molecular oxygen-containing gas at vapor phase, a complex oxide composition characterized by comprising (A) a complex oxide containing as essential components molybdenum, bismuth and iron, which is known per se as a catalyst for said vapor phase catalytic oxidation reaction, and (B) a complex oxide containing cerium and zirconium as the essential components, is provided.

According to the present invention, there is also provided, as a catalyst for producing unsaturated aldehyde and unsaturated carboxylic acid through oxidation of at least one compound selected from the group consisting of propylene, isobutylene, t-butanol and methyl-t-butyl ether with molecular oxygen or a molecular oxygen-containing gas at vapor phase, a complex oxide composition which is characterized by having a composition expressed by the following general formula (3):

$$Mo_aW_bBi_cFe_dCe_eZr_fA_gB_hC_iD_jE_kG_lO_x \qquad (3)$$

(wherein Mo is molybdenum; W is tungsten: Bi is bismuth; Fe is iron; Ce is cerium; Zr is zirconium; A is at least an element selected from nickel and cobalt; B is at least an element selected from alkali metals and thallium; C is at least an element selected from alkaline earth metals; D is at least an element selected from phosphorus, tellurium, antimony, tin, lead, niobium, manganese, arsenic and zinc; E is at least an element selected from silicon, aluminium and titanium; G is at least an element selected from the group consisting of lanthanoide series except cerium; yttrium, copper, indium, chromium and germanium; and O is oxygen; a, b, c, d, e, f, g, h, i, j, k, l and x denote the atomic ratios of Mo, W, Bi, Fe, Ce, Zr, A, B, C, D, E, G and O, respectively, and where a is 12, b is 0–10, c is 0.1–10, d is 0.1–20, e is 0.01–30, f is 0.01–42, g is 2–20, h is 0.001–10, i is 0–10, j is 0–4, k is 0–30, l is 0–7, and x is a numerical value determined by degree of oxidation of each of the elements)

and the cerium and zirconium therein forming a complex oxide.

According to the invention, furthermore, there is provided a process for producing unsaturated aldehyde and unsaturated carboxylic acid through vapor phase oxidation of at least one compound selected from the group consisting of propylene, isobutylene, t-butanol and methyl-t-butyl ether with molecular oxygen or a molecular oxygen-containing gas, in the presence of a catalyst, the process being characterized in that it uses the above-defined complex oxide composition as the catalyst.

EMBODIMENTS OF THE INVENTION

Catalyst (I) for unsaturated aldehyde and unsaturated carboxylic acid production according to the invention is a complex oxide composition which is characterized by comprising (A) a complex oxide containing as essential components molybdenum, bismuth and iron, which is known per se as a catalyst for producing unsaturated aldehyde and unsaturated carboxylic acid through said vapor phase catalytic oxidation reaction of propylene, isobutylene, t-butanol and methyl-t-butyl ether, and (B) a complex oxide containing cerium and zirconium as the essential components.

Catalyst (II) for unsaturated aldehyde and unsaturated carboxylic acid production according to another embodiment of the present invention is a complex oxide composition which is characterized by having the composition as expressed by above general formula (3), in which cerium and zirconium form a complex oxide.

First, the Catalyst (I) shall be explained. The component (A) corresponds to a catalyst containing molybdenum, bismuth and iron as the essential components, which is known as a catalyst for unsaturated aldehyde and unsaturated carboxylic acid production by vapor phase oxidation reaction of propylene, isobutylene, t-butanol or methyl-t-butyl ether. While any of known catalysts containing molybdenum, bismuth and iron as the essential components can be used as the component (A), those preferred are expressed by the following general formula (1):

$$Mo_aW_bBi_cFe_dA_eB_fC_gD_hE_iO_x \qquad (1)$$

(wherein Mo is molybdenum; W is tungsten; Bi is bismuth; Fe is iron; A is at least an element selected from nickel and cobalt; B is at least an element selected from alkali metals and thallium; C is at least an element selected from alkaline earth metals; D is at least an element selected from phosphorus, tellurium, antimony, tin, lead, niobium, manganese, arsenic and zinc; E is at least an element selected from silicon, aluminium and titanium;

and 0 is oxygen; a, b, c, d, e, f, g, h, i and x denote the atomic ratios of Mo, W, Bi, Fe, A, B, C, D, E and O, respectively; and where a is 12, b is 0–10, c is 0.1–10, d is 0.1–20, e is 2–20, f is 0.001–10, g is 0–10, h is 0–4, i is 0–30 and x is determined by degree of oxidation of each of the elements).

Method of preparing those catalysts is subject to no critical limitation, and the catalysts can be prepared by any known method. Kinds of the compounds containing the catalytic elements, which serve as the starting materials, are not critical but any oxides containing the catalytic elements or compounds capable of forming such oxides upon being calcined can be used. As the compounds which form oxides upon calcining, for example, hydroxides, metallic acids, nitrates, carbonates, ammonium salts, acetates and formates may be named. Compounds containing more than one of the elements are also useful. For instance, specific examples of molybdenum-containing compounds include molybdenum trioxide, ammonium paramolybdate, molybdic acid, phosphomolybdic acid and phosphovanadomolybdic acid.

Normally each prescribed amount of those starting compounds containing the component elements are, for example, suitably dissolved in an aqueous medium, heated under stirring, evaporated to dry solid and optionally pulverized to provide the intended component (A).

As the component (B), any complex oxide which contains cerium and zirconium as the essential components can be used. In particular, complex oxides which are expressed by the following general formula (2):

$$Ce_pZr_qF_rO_y \qquad (2)$$

(wherein Ce is cerium; Zr is zirconium; F is at least an element selected from the group consisting of lanthanoide series except cerium; yttrium, cobalt, nickel, copper, indium, tin, chromium and germanium; and O is oxygen; p, q, r and y denote the atomic ratios of Ce, Zr, F and O, respectively, p and q being optional numbers not including 0, r being a number satisfying the relationship $0 \leq r/(p+q) < 0.1$, and y being a number determined by degree of oxidation of each of the elements)

are conveniently used. More specifically, when p=1, $0.01 \leq q \leq 99$, $0 \leq r < 10$, preferably $0.05 \leq q \leq r19$ and $0 - \leq r < 2$.

Method of preparing complex oxides containing cerium and zirconium as the essential components is subject to no critical limitation, and they can be prepared by any known method. Kinds of the compounds containing the named elements, which serve as the starting materials, are not critical but any oxides containing the named elements or compounds capable of forming such oxides upon being calcined can be used. As the compounds which form oxides upon being calcined, for example, hydroxides, metallic acids, nitrates, carbonates, ammonium salts, acetates and formates may be named. For example, as a specific example of cerium-containing compound, cerium nitrate may be named.

Of the complex oxides expressed by the general formula (2), those in which cerium oxide and zirconium oxide are at least partially forming a solid solution are conveniently used. In particular, those in which the molar ratio of $CeO_2/ZrO_2$ is within a range from 1/99—99/1, preferably 5/95—95/5 are preferred. Furthermore, in the present invention it is essential that the cerium and zirconium are forming a complex oxide. Use of a simple mixture of cerium oxide and zirconium oxide cannot achieve the objects of the present invention.

The component (B) is not limited to complex oxides of cerium and zirconium only, but it may contain the element(s) expressed by the symbol F in general formula (2) in the form of complex oxide. Typical methods for preparation of the component (B) include: (1) mix an aqueous solution of water-soluble cerium salt with that of water-soluble zirconium salt, dry and calcine the same; (2) react cerium oxide with zirconium oxide at solid phase; and (3) impregnate cerium oxide with aqueous solution of water-soluble zirconium salt, dry and calcine the same. The calcining temperature is normally 200–800° C., preferably 300–700° C. Upon such calcining, complex oxide containing cerium and zirconium is formed.

The ratio of component (B) to component (A) (as converted to oxides) is normally 0.5–30% by weight, preferably 1–20% by weight. When it is too low, the intended effect of adding component (B) cannot be attained, while if it is too high, yield drops as the production amounts of the intended unsaturated aldehyde and unsaturated carboxylic acid reduce and those of $CO_2$ and Co increase.

The catalyst of the present invention can be used by itself or may be supported on inert carriers such as alumina, silica-alumina, silicon carbide, titanium dioxide, magnesium oxide, aluminium sponge and the like. In that occasion inorganic fibers such as glass fiber and various kinds of whiskers, which are generally well known for their effect of improving strength and attrition resistance of catalyst may be added. Also for controlling the catalyst properties with good reproducibility, additives generally known as powder binder such as ammonium nitrate, cellulose, starch, polyvinyl alcohol, stearic acid and the like may be used.

Shape of the catalyst is not critical, which may be any optional form such as pellets, spheres, columns, rings, tablets and the like. Their average diameter is 1–15 mm, preferably 3–10 mm.

Method for preparing the catalyst containing components (A) and (B) is subject to no critical limitation, and any optional method can be used. For example, advancedly prepared powders of the respective components are mixed, optionally using ball mill or the like to effect intimate mixing; or advancedly prepared component (B) is dispersed in component (A) under preparation, at an optional stage.

It is generally preferred for catalyst (I) to be used as molded catalyst as prepared by a process comprising thoroughly mixing the components (A) and (B); imparting to the mixture a desired shape, optionally adding water or the like as a molding aid; and calcining the same in an air stream at 300–600° C., preferably 350–550° C., for about 1–10 hours, preferably about 2–8 hours.

Catalyst (II) for producing unsaturated aldehyde and unsaturated carboxylic acid according to the present invention has the composition as expressed by the general formula (3) above, in which cerium and zirconium are forming a complex oxide. That is, catalyst (II) contains cerium and zirconium in the form of a complex oxide containing said two elements. A typical method for preparing this catalyst (II) is, similar to the one for preparing catalyst (I), to blend advancedly prepared components (A) and (B). Methods for preparing components (A) and (B), respectively, are same as already described.

Production of unsaturated aldehyde and unsaturated carboxylic acid according to the present invention can be carried out under the conditions normally employed in conventional methods for producing unsaturated aldehyde and unsaturated carboxylic acid from propylene, isobutylene, t-butanol or methyl-t-butyl ether or their mixtures, by vapor phase oxidation reaction, except that a catalyst of the present invention for producing unsaturated aldehyde and unsaturated carboxylic acid is used as the catalyst.

For example, a gaseous mixture comprising 1–10 vol. %, preferably 2–8 vol. % of at least one starting compound selected from the group consisting of propylene, isobutylene, t-butanol and methyl-t-butyl ether; 1–10 times by volume, preferably 1–8 times by volume, of the starting compound of molecular oxygen; and inert gas as a diluent, such as nitrogen, carbon dioxide, steam and the like (use of, in particular, steam is advantageous for improving the yield of the object product, because it inhibits formation of side products), is contacted with a catalyst of the present invention at temperatures ranging from 250 to 450° C., preferably from 280 to 420° C., under pressures ranging from normal to 10 atmospheres, preferably from normal to 8 atmospheres, and at a space velocity ranging from 300 to 5,000 hr$^{-1}$ (STP), preferably from 500 to 4,000 hr$^{-1}$ (STP).

According to the process of the present invention, acrolein and acrylic acid are produced from propylene; methacrolein and methacrylic acid, from isobutylene; methacrolein and methacrylic acid, from t-butanol; and methacrolein and methacrylic acid, from methyl-t-butyl ether. Obviously, it is possible to vary the production ratios of such unsaturated aldehyde and unsaturated carboxylic acid, by suitably changing the reaction conditions. For example, where propylene is used as starting compound, mixtures of acrolein as the major component and acrylic acid as the minor component can be obtained as the product.

The action of the component (B) in the catalyst of the present invention is presumed to be as follows: highly dispersible zirconium oxide inhibits aggregation of cerium oxide, to maintain the latter's promoting function to favorably absorb and release oxygen during the reaction, and whereby the oxidation reaction of propylene, isobutylene, t-butanol or methyl-t-butyl ether is accelerated, in consequence increasing the catalytic activity. Furthermore, irreversible activity deterioration in the component (A) complex oxide due to overreduction with time is inhibited (i.e., stability of the complex oxide is increased), resulting in prolongation of the catalyst life. Such increased catalytic activity and extended catalyst life inhibit the rise in the reaction temperature with time, to reduce scattering about of molybdenum at the hot spot. Needless to say, the present invention however is not restricted by such theoretical observation.

EFFECT OF THE PRESENT INVENTION

Use of the catalyst of the present invention in vapor phase oxidation reaction of at least one compound selected from the group consisting of propylene, isobutylene, t-butanol or methyl-t-butyl ether enables production of unsaturated aldehyde and unsaturated carboxylic acid at high yield. Because the catalyst of the present invention has a long life, it enables stable operation over prolonged period. Furthermore, the catalyst of the present invention enables stable operation over prolonged period also for heavy-load operation aiming at high productivity.

EXAMPLES

Hereinafter the present invention is explained more specifically, referring to working Examples, it being understood that the invention is not limited thereto. In the following Examples and Comparative Examples, the conversion, selectivity and one-pass yield have the following definitions.

Conversion (mol %)=
(mol number of reacted starting compound/mol number of supplied starting compound)×100

Selectivity (mol %)=
(total mol number of formed unsaturated aldehyde and unsaturated carboxylic acid/mol number of reacted starting compound)×100

One-pass yield (mol %)=
(total mol number of formed unsaturated aldehyde and unsaturated carboxylic acid/mol number of suppled starting compound)×100

Example 1

<Catalyst preparation>

Into 2 liters of heated ion-exchange water, 1500 g of ammonium paramolybdate and 382.4 g of ammonium paratungstate were added and dissolved under stirring. Separately, 1648.5 g of cobalt nitrate, 429.1 g of ferric nitrate and 69.0 g of cesium nitrate were dissolved in 1 liter of ion-exchange water; and 515.2 g of bismuth nitrate was dissolved in an aqueous nitric acid consisting of 300 ml of ion-exchange water and 50 ml of conc. nitric acid. These two aqueous solutions were dropwisely added to the first aqueous solution which was separately prepared as above and mixed, followed by addition of 212.7 g of silica sol of 20% by weight in concentration. The slurry resulting from mixing the system was heated under stirring to dry solid and pulverized to provide a powder (powder A). Separately, 37.8 g of zirconium hydroxynitrate was completely dissolved in 1 liter of ion-exchange water, and into the solution aqueous ammonia was gradually added under stirring to precipitate hydrated zirconia sol. Then an aqueous solution of 245.9 g of cerium nitrate in 1 liter of ion-exchange water was added, and into the mixture of the solutions aqueous ammonia was further gradually added dropwise under stirring, until pH rose to 10. The resulting precipitate was filtered, washed with water, dried and calcined at 400° C. for 2 hours to provide a powder (powder B). Powder B was added to powder A and mixed well. Water was added to the mixture as a molding aid, and the mixture was molded into pellets of each 6 mm in outer diameter and 6.6 mm in length, which were dried and then calcined in an air stream at 500° C. for 6 hours to provide catalyst (1). The elementary composition of this catalyst (1) was as follows, in terms of atomic ratio (excepting oxygen, as in all of the following Examples):

$Mo_{12}W_2Bi_{1.5}Fe_{1.5}Ce_{0.8}Zr_{0.2}Co_8Cs_{0.5}Si_1$

It was confirmed by X-ray diffraction analysis that the cerium and zirconium in powder B were forming a complex oxide.

<Oxidation reaction>

A steel reactor of 25 mm in diameter was charged with 1200 ml of catalyst (1), and into which a gaseous mixture comprising 6 vol. % of isobutylene, 13 vol. % of oxygen, 8 vol. % steam and 73 vol. % of nitrogen was introduced. The oxidation reaction was conducted at a temperature of 340° C. and a space velocity of 1500 hr$^{-1}$ (STP). The result was as shown in Table 1.

Comparative Example 1

<Catalyst preparation>

Catalyst (2) was prepared in the same manner as in Example 1, except that powder B was not added.

<Oxidation reaction>

In Example 1, the oxidation reaction was conducted under identical conditions with those in Example 1, except that catalyst (2) was used in place of catalyst (1). The result was as shown in Table 1.

Upon comparing Example 1 with Comparative Example 1, it is understood that catalyst (1) of the present invention excels over the control catalyst (2) in catalytic activity.

Example 2

According to Example 1, the oxidation reaction was continued for 4000 hours. The result after the 4000 hours' operation was as shown in Table 1.

As indicated in Table 1, the drop in conversion after 4000 hours' oxidation reaction was minor and there was almost no decrease in the yield. From this result it can be understood that the use of catalyst (1) enables stable continuation of the oxidation reaction over a long period.

Comparative Example 2

According to Comparative Example 1, the oxidation reaction was continued for 4000 hours. The result after the 4000 hours' operation was as shown in Table 1.

Upon comparison of Example 2 with Comparative Example 2, it can be understood that the control catalyst (2) has a problem of short catalyst life, and when it is used in the reaction for many hours, decreases in conversion and yield are notable.

TABLE 1

| | Catalyst No. | Reaction Temp. (° C.) | Isobutylene Conversion (mol %) | Total Selectivity (mol %) | Total One-pass Yield (mol %) | Remarks |
|---|---|---|---|---|---|---|
| Example 1 | (1) | 340 | 99.1 | 87.5 | 86.8 | |
| Comparative Example 1 | (2) | 340 | 96.8 | 87.5 | 84.7 | |
| Example 2 | (1) | 340 | 98.2 | 87.9 | 86.3 | After 4,000 hours |
| Comparative Example 2 | (2) | 340 | 94.5 | 87.5 | 82.7 | After 4,000 hours |

Example 3

<Catalyst preparation>

Into 2 liters of heated ion-exchange water, 1500 g of ammonium paramolybdate and 191.2 g of ammonium paratungstate were added and dissolved under stirring. Separately, 1236.4 g of cobalt nitrate, 205.9 g of nickel nitrate, 429.1 g of ferric nitrate and 82.8 g of cesium nitrate were dissolved in 1 liter of ion-exchange water; and 618.2 g of bismuth nitrate was dissolved in an aqueous nitric acid solution consisting of 300 ml of ion-exchange water and 50 ml of conc. nitric acid. These two aqueous solutions were dropwisely added to the first aqueous solution which was separately prepared and mixed, followed by addition of 212.7 g of silica sol of 20% by weight in concentration. The whole system was mixed to form a slurry (slurry A). Separately, 151.3 g of zirconium hydroxynitrate was completely dissolved in 1 liter of ion-exchange water, and into that solution aqueous ammonia was gradually added under stirring to precipitate hydrated zirconia sol, followed by addition of an aqueous solution of 61.5 g of cerium nitrate in 1 liter of ion-exchange water. Then aqueous ammonia was further slowly added to the mixture of the solutions dropwise under stirring until pH rose to 10. The resulting precipitate was filtered, washed with water, dried and calcined at 500° C. for 2 hours to provide a powder (powder B). This powder B was added to slurry A, mixed, evaporated to dry solid and pulverized. Water was added to the resulting powder as a molding aid, and the mixture was molded into pellets of each 6 mm in outer diameter and 6.6 mm in length, which were dried and calcined in an air stream at 500° C. for 6 hours to provide catalyst (3). The elementary composition of this catalyst (3) was as follows, in terms of atomic ratio:

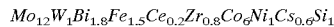

$Mo_{12}W_1Bi_{1.8}Fe_{1.5}Ce_{0.2}Zr_{0.8}Co_6Ni_1Cs_{0.6}Si_1$

It was confirmed by X-ray diffraction analysis that the cerium and zirconium in powder B were forming a complex oxide.

<Oxidation reaction>

In Example 1, the oxidation reaction was conducted under identical conditions with those in Example 1, except that catalyst (3) was used in place of catalyst (1). The result was as shown in Table 2.

Comparative Example 3

<Catalyst preparation>

Catalyst (4) was prepared in the identical manner with the catalyst preparation in Example 3, except that the powder B was provided by mixing 69.8 g of a powder formed by 2 hours' calcining at 500° C. of the hydrated zirconia sol precipitate derived from zirconium hydroxynitrate, with 24.4 g of a commercial cerium oxide powder ($CeO_2$, specific surface area: 100 $m^2$).

<Oxidation reaction>

In Example 3, the oxidation reaction was conducted under identical conditions with those in Example 3, except that catalyst (4) was used in place of catalyst (3). The result was as shown in Table 2.

Upon comparing Example 3 with Comparative Example 3, it is understood that the catalyst (3) according to the invention excels in catalytic activity over the control catalyst (4).

Example 4 According to Example 3, the oxidation reaction was continued for 4000 hours. The result after the 4000 hours' operation was as shown in Table 2.

As indicated in Table 2, the drop in conversion after 4000 hours' oxidation reaction was minor and there was almost no decrease in the yield. From this result it can be understood that the use of catalyst (3) enabled stable continuation of the oxidation reaction over a long period.

Comparative Example 4

According to Comparative Example 3, the oxidation reaction was continued for 4000 hours. The result after the 4000 hours' operation was as shown in Table 2.

Upon comparison of Example 4 with Comparative Example 4, it can be understood that the control catalyst (4) has a problem of short catalyst life, and when it is used in the reaction for many hours,-decreases in conversion and yield are notable.

Example 6

The oxidation reaction of Example 3 was repeated except that the isobutylene and nitrogen contents in the gaseous mixture fed into the reactor for the oxidation reaction were changed to 7.5 vol. % and 71.5 vol. %, respectively. The result was as shown in Table 3.

Comparative Example 6

The oxidation reaction of Example 6 was repeated except that catalyst (3) was replaced with catalyst (4). The result was as shown in Table 3.

Upon comparing Example 6 with Comparative Example 6, it is understood that catalyst (3) of the present invention excels over the control catalyst (4) in both activity level and yield, also under high isobutylene concentration condition.

TABLE 3

|  | Catalyst No. | Reaction Temp. (° C.) | Isobutylene Conversion (mol %) | Total Selectivity (mol %) | Total One-pass Yield (mol %) |
| --- | --- | --- | --- | --- | --- |
| Example 5 | (3) | 360 | 98.9 | 88.2 | 87.2 |
| Comparative Example 5 | (4) | 360 | 96.4 | 88.1 | 84.9 |
| Example 6 | (3) | 340 | 98.8 | 87.6 | 86.5 |
| Comparative Example 6 | (4) | 340 | 96.4 | 87.5 | 84.4 |

Example 7

<Catalyst preparation>

Catalyst (5) was prepared in the identical manner with Example 3, except that the powder B was prepared with the amounts of the zirconium hydroxynitrate and cerium nitrate varied, yttrium oxide was added and the calcining was conducted at 650° C. for 1 hour. The elementary composition of this catalyst (5) was as follows, in terms of atomic ratio:

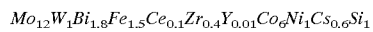

$Mo_{12}W_1Bi_{1.8}Fe_{1.5}Ce_{0.1}Zr_{0.4}Y_{0.01}Co_6Ni_1Cs_{0.6}Si_1$

It was confirmed by X-ray diffraction analysis that the cerium, zirconium and yttrium were forming a complex oxide in powder B.

TABLE 2

|  | Catalyst No. | Reaction Temp. (° C.) | Isobutylene Conversion (mol %) | Total Selectivity (mol %) | Total One-pass Yield (mol %) | Remarks |
| --- | --- | --- | --- | --- | --- | --- |
| Example 3 | (3) | 340 | 99.0 | 87.4 | 86.5 |  |
| Comparative Example 3 | (4) | 340 | 96.7 | 87.4 | 84.5 |  |
| Example 4 | (3) | 340 | 98.2 | 87.6 | 86.0 | After 4,000 hours |
| Comparative Example 4 | (4) | 340 | 94.1 | 87.5 | 82.3 | After 4,000 hours |

Example 5

Example 3 was repeated except that the oxidation reaction was carried out at 360° C. and at a space velocity of 2500 $hr^{-1}$ (STP). The result was as shown in Table 3.

Comparative Example 5

The oxidation reaction of Example 5 was repeated except that catalyst (4) was used in place of catalyst (3). The result was as shown in Table 3.

Upon comparing Example 5 with Comparative Example 5, it is understood that catalyst (3) of the present invention excels over the control catalyst (4) in the activity level and yield, also under high space velocity condition.

<Oxidation reaction>

The oxidation reaction was conducted in the identical manner with Example 3, except that catalyst (5) was used in place of catalyst (3). The result was as shown in Table 4.

Examples 814 15

<Catalyst preparation>

Catalysts (6)–(13) were prepared in the identical manner with Example 7, except that the powder B was prepared with the amounts of the zirconium hydroxynitrate and cerium nitrate varied and that yttrium oxide was replaced with an oxide containing the element as indicated in Table 4 for each Example.

<Oxidation reaction>

The oxidation reaction of Example 7 was repeated except that catalyst (5) was replaced with catalysts (6)–(13) as indicated for each Example. The results were as shown in Table 4.

TABLE 4

| | Catalyst Composition (atomic ratio excepting oxygen) $Mo_{12}W_1Bi_{1.8}Fe_{1.5}Co_6Ni_1Cs_{0.6}Si_1$ | | | Catalyst No. | Reaction Temp. (°C.) | Isobutylene Conversion (mol %) | Total Selectivity (mol %) | Total One-pass Yield (mol %) |
|---|---|---|---|---|---|---|---|---|
| | Ce | Zr | F | | | | | |
| Example 7 | 0.1 | 0.4 | Y = 0.01 | (5) | 340 | 99.0 | 87.5 | 86.6 |
| Example 8 | 0.2 | 0.8 | La = 0.02 | (6) | 340 | 99.1 | 87.2 | 86.4 |
| Example 9 | 0.6 | 0.4 | Pr = 0.02 | (7) | 340 | 99.1 | 87.1 | 86.3 |
| Example 10 | 0.4 | 0.6 | Sm = 0.02 | (8) | 340 | 99.0 | 87.3 | 86.4 |
| Example 11 | 0.3 | 0.7 | Nd = 0.01 | (9) | 340 | 98.9 | 87.4 | 86.4 |
| Example 12 | 0.2 | 0.8 | In = 0.01 | (10) | 340 | 98.9 | 87.2 | 86.2 |
| Example 13 | 0.3 | 0.7 | Ni = 0.01 | (11) | 340 | 99.2 | 87.1 | 86.4 |
| Example 14 | 0.5 | 0.5 | Co = 0.01 | (12) | 340 | 99.1 | 87.1 | 86.3 |
| Example 15 | 0.3 | 0.7 | Cu = 0.01 | (13) | 340 | 99.1 | 87.0 | 86.2 |

Example 16

The oxidation reaction of Example 3 was repeated except that t-butanol was used as the starting gas. The result was as shown in Table 5.

Comparative Example 7

The oxidation reaction of Example 16 was repeated except that catalyst (3) was replaced with catalyst (4). The result was as shown in Table 5.

TABLE 5

| | Catalyst No. | Reaction Temp. (°C.) | t-Butanol Conversion (mol %) | Total Selectivity (mol %) | Total One-pass Yield (mol %) |
|---|---|---|---|---|---|
| Example 16 | (3) | 340 | 100 | 86.6 | 86.6 |
| Comparative Example 7 | (4) | 340 | 100 | 84.9 | 84.9 |

Example 17

The oxidation reaction of Example 3 was repeated except that a gaseous mixture of 5 vol. % of methyl-t-butyl ether (MTBE), 13 vol. % of oxygen, 8 vol. % of steam and 74 vol. % of nitrogen was used as the starting gas, the reaction temperature was changed to 360° C., and the space velocity was changed to 1100 hr$^{-1}$ (STP). The result was as shown in Table 6.

Comparative Example 8

The oxidation reaction of Example 17 was repeated except that catalyst (3) was replaced with catalyst (4). The result was as shown in Table 6.

TABLE 6

| | Catalyst No. | Reaction Temp. (°C.) | MTBE Conversion (mol %) | Total Selectivity (mol %) | Total One-pass Yield (mol %) |
|---|---|---|---|---|---|
| Example 17 | (3) | 360 | 99.0 | 86.5 | 85.6 |
| Comparative Example 8 | (4) | 360 | 97.8 | 86.4 | 84.5 |

Example 18

<Catalyst preparation>

Into 2 liters of heated ion-exchange water, 1500 g of ammonium paramolybdate and 286.8 g of ammonium paratungstate were added and dissolved under stirring.

Separately, 1030.3 g of cobalt nitrate, 343.3 g of ferric nitrate and 4.3 g of potassium nitrate were dissolved in 1 liter of ion-exchange water; and 412.1 g of bismuth nitrate was dissolved in an aqueous nitric acid solution consisting of 300 ml of ion-exchange water and 50 ml of conc. nitric acid. These two aqueous solutions were dropwisely added to the first aqueous solution which was separately prepared and mixed, followed by addition of 276.5 g of silica sol of 20% by weight in concentration. The whole system was mixed to form a slurry (slurry A). Separately, 75.7 g of zirconium hydroxynitrate was completely dissolved in 1 liter of ion-exchange water, and into that solution aqueous ammonia was gradually added under stirring to precipitate hydrated zirconia sol, followed by addition of an aqueous solution of 30.7 g of cerium nitrate in 1 liter of ion-exchange water. Then aqueous ammonia was further slowly added to the mixture of the solutions dropwise under stirring until pH rose to 10. The resulting precipitate was filtered, washed with water, dried and calcined at 550° C. for 2 hours to provide a powder (powder B). This Powder B was added to slurry A, mixed, evaporated to dry solid and pulverized. Water was added to the resulting powder as a molding aid, and the mixture was molded into pellets of each 6 mm in outer diameter and 6.6 mm in length, which were dried and calcined in an air stream at 450° C. for 6 hours to provide catalyst (14). The elementary composition of this catalyst (14) was as follows, in terms of atomic ratio:

$$Mo_{12}W_{1.5}Bi_{1.2}Fe_{1.2}Ce_{0.1}Zr_{0.4}Co_5K_{0.06}Si_{1.3}$$

It was confirmed by X-ray diffraction analysis that the cerium and zirconium in powder B were forming a complex oxide.

<Oxidation reaction>

A steel reactor of 25 mm in diameter was charged with 1200 ml of catalyst (14), and into which a gaseous mixture comprising 6 vol. % of propylene, 12 vol. % of oxygen, 10 vol. of % steam and 72 vol. % of nitrogen was introduced. The oxidation reaction was conducted at 310° C. and space velocity of 2000 hr$^{-1}$ (STP). The result was as shown in Table 7.

Comparative Example 9

<Catalyst preparation>

Catalyst (15) was prepared in the same manner as in Example 18, except that powder B was not added.

<Oxidation reaction>

The oxidation reaction of Example 18 was repeated except that catalyst (15) was used in place of catalyst (14). The result was as shown in Table 7.

Upon comparing Example 18 with Comparative Example 9, it is understood that catalyst (14) of the present invention excels over the control catalyst (15) in catalytic activity.

Example 19

According to Example 18, the oxidation reaction was continued for 4000 hours. The result after the 4000 hours' operation was as shown in Table 7.

As indicated in Table 7, the drop in conversion after 4000 hours' oxidation reaction was minor and there was almost no decrease in the yield. From this result it can be understood that the use of catalyst (14) enables stable continuation of the oxidation reaction over a long period.

Comparative Example 10

According to Comparative Example 9, the oxidation reaction was continued for 4000 hours. The result after the 4000 hours' operation was as shown in Table 7.

Upon comparison of Example 19 with Comparative Example 10, it can be understood that the control catalyst (15) has a problem of short catalyst life, and when it is used in the reaction for many hours, decreases in conversion and yield are notable.

5. A catalyst according to claim 1, wherein component (A) is a complex oxide expressed by the following general formula (1):

$$Mo_aW_bBi_cFe_dA_eB_fC_gD_hE_iO_x \quad (1)$$

wherein Mo represents molybdenum; W represents tungsten, Bi represents bismuth, Fe represents iron, A represents at least one of nickel and cobalt, B represents at least one of alkali metal and thallium, C represents at least one alkaline earth metal element, D represents at least one element selected from the group consisting of phosphorus, tellurium, antimony, tin, lead, niobium, manganese, arsenic, and zinc, E represents at least one element selected from the group consisting of titanium, silicon and aluminum; and O represents oxygen; a, b, c, d, e, f, g, h, i and x denote the atomic ratios aluminum; and O represents oxygen; a, b, c, d, e, f, g, h, i and x denote the atomic ratios of Mo, W, Bi, Fe, A, B, C, D, E and 0, respectively; and when a is 12, b is 0–10, c is 0.1–10, d is 0.1–20, e is 2–20, f is 0.001–10, g is 0–10, h is 0–4, i is 0–30; and x is determined by degree of oxidation of each of the elements.

6. A catalyst according to claim 1 or claim 5, wherein component (B) is a complex oxide expressed by the following general formula (2):

$$Ce_pZr_qF_rO_y \quad (2)$$

wherein Ce represents cerium; Zr represents zirconium; F represents at least one element selected from the group

TABLE 7

| | Catalyst No. | Reaction Temp. (° C.) | Propylene Conversion (mol %) | Total Selectivity (mol %) | Total One-pass Yield (mol %) | Remarks |
|---|---|---|---|---|---|---|
| Example 18 | (14) | 310 | 98.6 | 94.2 | 92.9 | |
| Comparative Example 9 | (15) | 310 | 96.1 | 94.0 | 90.3 | |
| Example 19 | (14) | 310 | 98.0 | 94.3 | 92.4 | After 4,000 hours |
| Comparative Example 10 | (15) | 310 | 93.9 | 93.7 | 88.0 | After 4,000 hours |

What is claimed is:

1. A catalyst useful for catalyzing the oxidation and/or oxidative dehydrogenation of propylene, isobutylene, t-butanol, or methyl-t-butyl ether with molecular oxygen or a molecular oxygen-containing gas to produce the corresponding unsaturated aldehyde and unsaturated carboxylic acid, said catalyst composition comprising (A) a complex oxide comprising molybdenum, bismuth and iron, as essential elements and, which is effective for catalyzing a vapor phase catalytic oxidation and/or vapor phase oxidative dehydrogenation reaction of propylene, isobutylene, t-butanol or methyl-t-butyl ether, to produce the corresponding unsaturated aldehyde and unsaturated carboxylic acid, and (B) a complex oxide containing cerium and zirconium as essential components.

2. The catalyst composition according to claim 1, wherein in the complex oxide containing cerium and zirconium, the molar ratio, CeO$_2$/ZrO$_2$ is in the range of from 5/95 to 95/5.

3. The catalyst composition according to claim 1 or claim 2, wherein the ratio, by weight, of the complex oxide (A) to the complex oxide (B) is from 0.5 to 30%.

4. The catalyst composition according to claim 1 or claim 2, wherein the ratio, by weight, of the complex oxide (A) to the complex oxide (B) is from 1 to 20%.

consisting of lanthanoide series elements other than cerium; yttrium, cobalt, nickel, copper, indium, tin, chromium and germanium; and O represents oxygen; p, q, r and y denote the atomic ratios of Ce, Zr, F and 0, respectively, p and q being positive numbers, r being a number satisfying the relationship $$0 \leq r/(p+q) < 0.1,$$

and y being a number determined by degree of oxidation of each of the elements.

7. A process for producing unsaturated aldehyde and unsaturated carboxylic acid through vapor phase oxidation of at least one compound selected from the group consisting of propylene, isobutylene, t-butanol and methyl-t-butyl ether with molecular oxygen or a molecular oxygen-containing gas, in the presence of a catalyst, the process being characterized in that it uses the catalyst as defined by claim 1 and 3.

8. A catalyst useful for catalyzing the oxidation of propylene, isobutylene, t-butanol or methyl-t-butyl or ether with molecular oxygen or a molecular oxygen-containing gas to produce the corresponding unsaturated aldehyde and unsaturated carboxylic acid, said catalyst having a composition expressed by the following general formula (3):

$$Mo_aW_bBi_cFe_dCe_eZr_fA_gB_hC_iD_jE_kG_lO_x \quad (3)$$

wherein Mo represents molybdenum; W represents tungsten, Bi represents bismuth, Fe represents iron, Ce represents cerium; Zr represents zirconium; A represents at least one of nickel and cobalt; B represents at least one element selected from the group consisting of alkali metals and thallium; C represents at least one element selected from alkaline earth metal elements; D represents at least one element selected from the group consisting of phosphorus, tellurium, antimony, tin, lead, niobium, manganese, arsenic and zinc; E represents at least one element selected from the group consisting of silicon, aluminum, and titanium; G represents at least one element selected from the group consisting of lanthanoide series elements other than cerium; yttrium, copper, indium, chromium, and germanium; and 0 represents oxygen; a, b, c, d, e, f, g, h, i, j, k, l and x denote the atomic ratios of Mo, W, Bi, Fe, Ce, Zr, A, B, C, D, E, G and 0, respectively; and when a is 12, b is 0–10, c is 0.1–10, d is 0.1–20, e is 0.01–30, f is 0.01–42, g is 2–20, h is 0.001–10, i is 0–10, j is 0–4, k is 0–30, l is 0–7, and x is a numerical value determined by degree of oxidation of each of the elements; and the cerium and zirconium therein forming a complex oxide.

* * * * *